(12) United States Patent
Gidwani et al.

(10) Patent No.: US 6,270,797 B1
(45) Date of Patent: Aug. 7, 2001

(54) SUSTAINED RELEASE PHARMACEUTICAL COMPOSITION CONTAINING GLIPIZIDE AND METHOD FOR PRODUCING SAME

(75) Inventors: Suresh Kumar Gidwani; Purushottam Singnurkar; Prashant Kumar Tewari, all of Mumbai (IN)

(73) Assignee: USV Limited, Mumbai (IN)

( * ) Notice: Subject to any disclaimer, the term of this patent is extended or adjusted under 35 U.S.C. 154(b) by 0 days.

(21) Appl. No.: 09/573,290

(22) Filed: May 18, 2000

(51) Int. Cl.[7] ..................................................... A61K 9/52
(52) U.S. Cl. ..................... 424/457; 424/451; 424/452; 424/464; 424/465; 424/468; 424/469; 424/470; 424/489; 424/501
(58) Field of Search ..................... 424/451, 452, 424/457, 458, 464, 465, 468, 474, 480, 481, 489, 490, 494, 495, 496, 498; 514/866

(56) References Cited

U.S. PATENT DOCUMENTS

| | | | |
|---|---|---|---|
| 5,591,454 | * | 1/1997 | Kuczynski et al. ................. 424/486 |
| 5,654,005 | * | 8/1997 | Chen et al. ........................... 424/480 |
| 5,952,356 | * | 9/1999 | Ikeda et al. .......................... 514/340 |
| 6,031,004 | * | 2/2000 | Timmins et al. ..................... 514/635 |

* cited by examiner

Primary Examiner—Thurman K. Page
Assistant Examiner—Liliana Di Nola-Baron
(74) Attorney, Agent, or Firm—Cobrin & Gittes

(57) ABSTRACT

One aspect of the invention resides in a monolithic sustained release composition of glipizide for patients with non-insulin dependent diabetes mellitus that exhibits a breakdown after ingestion by a patient in conformity with a zero-order kinetic. The present invention provides a composition of a glipizide and a hydrocolloid forming agent and optimally other auxiliary excipients for the sustained release of glipizide. It is preferable that the hydrophilic material comprises at least 50% by weight of the composition. The present invention is also directed to the process for producing the composition. One aspect of this process includes the steps of granulating glipizide, a hydrophilic material and a diluent, drying the granulated product and lubricating the product with a flow regulating agent and lubricant.

6 Claims, 4 Drawing Sheets

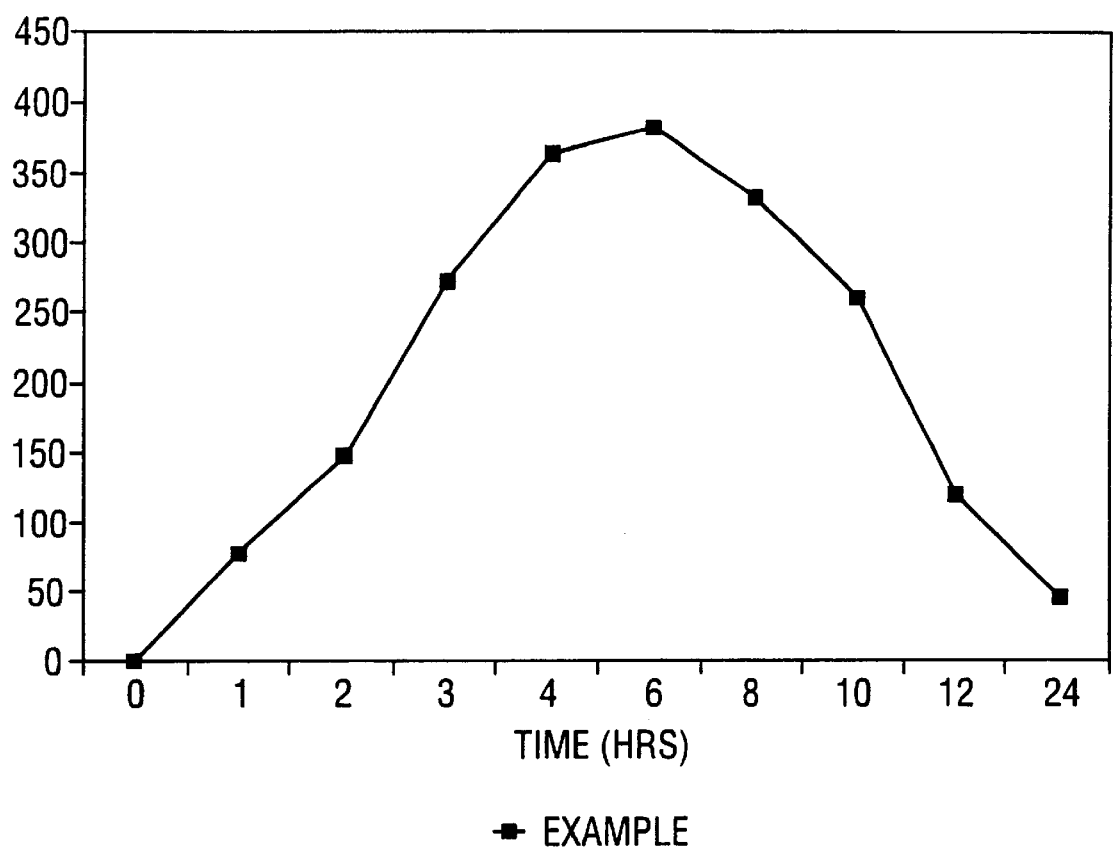

SUSTAINED RELEASE PHARMACEUTICAL COMPOSITION CONTAINING GLIPIZIDE AND METHOD FOR PRODUCING SAME

CROSS-REFERENCE TO RELATED PATENT APPLICATIONS

STATEMENT REGARDING FEDERALLY SPONSORED RESEARCH OR DEVELOPMENT

Not Applicable.

BACKGROUND OF THE INVENTION

1. Field of The Invention

The present invention relates to a sustained release pharmaceutical composition for delivering glipizide over a prolonged period of time. The invention uses glipizide with a hydrocolloid forming agent and other substances for the sustained release of glipizide. The present invention is also directed to a method for producing the sustained release composition.

2. Description of Related Art

Glipizide is an oral blood-glucose lowering drug that is used to manage hyperglycemia in patients with non-insulin dependent diabetes mellitus. Glipizide stimulates insulin secretion from the beta cells of pancreatic-islet tissue, increases the concentration of insulin in the pancreatic vein, and may increase the number of insulin receptors.

Glipizide (1-cyclohexyl-3-[[p-[2-(5-methylpyrazinecarboxamido) ethyl]phenyl]sulfonyl]urea), is an oral blood glucose lowering drug within the sulfonylurea class. Glipizide is generally a white, odorless compound. It is insoluble in water and alcohol, has a molecular weight of 445.55 and a pKa of 5.9.

Monolithic systems (e.g. tablets) composed of hydrophilic and/or hydrophobic polymers and other excipients are commonly used for manufacturing sustained release dosage compositions of glipizide. Such systems, however, often result in a first order (non-linear) kinetic release of glipizide. Glipizide is disproportionately released quickly after a patient ingests the sustained release glipizide composition, which results in a spike in the level of medication present in the patient's blood stream. This results in an uneven and inconsistent dosage of glipizide during the beginning of the prolonged period of time as compared to the latter portion of the prolonged period and this presents a significant drawback because diabetic patients can suffer various side effects from experiencing sudden spikes of glipizide.

U.S. Pat. No. 5,945,125 (the "'125 patent") naming Kim Chemg-ju as inventor, describes a process of manufacturing a controlled release tablet with a water swellable polymer, non-crosslinked polyethylene oxide, with an average molecular weight in the range of 900,000 to 5,000,000. The water swellable polymer is chosen such that the swelling rate of the polymer is equal to the dissolution rate of the swollen polymer. The '125 patent is generally directed to controlled release compositions. Although the '125 patent mentions glipizide as one of several drugs that may be used therewith, it does not particularize the formulation and in vivo release profile for glipizide. Yet, the '125 patent does discuss release profiles, in greater detail, for other pharmaceutical drugs mentioned therein.

Glucotrol-XL® is a registered trademark of Pfizer Inc., for glipizide-GITS (Gastrointestinal Therapeutic System). Glucotrol-XL® extended release tablets containing 2.5 to 20 mg glipizide, are commercially available to the public by prescription. The extended release of Glucotrol-XL® tablets is based on the osmotic and hydrostatic pressure system for drug release. However, these tablets typically possess lag times of 1 to 2 hours before the drug is released into the circulatory or endocrine system of the patient. The lag times may vary depending on the volume of fluids available in the patient's gastrointestinal (G.I.) tract at the time of administration of the drug. This is because the release of the drug is dependent upon hydration and osmotic pressure generation. As water from the G.I. tract enters the glipizide-GITS tablet, pressure increases in the osmotic layer of the tablet and pushes against the drug layer of the tablet, thereby releasing glipizide into the gastrointestinal lumen.

The technology to commercially manufacture Glucotrol-XL® is complicated and costly. It is complicated because the process requires manufacturing a bilayer tablet with a drug compartment (an active layer) and an osmotic compartment (pharmacologically inert). The tablet is then coated with a semipermeable membrane polymer and an aperture is laser drilled on the drug compartment side for drug release. A further film coating is then applied. This process is costly because each of the steps of manufacture requires specialized manufacturing equipment whose cost can exceed one million dollars. In addition, a great amount of time and precision is required to produce the Glucotrol-XL® tablets.

Studies by Berelowitz M, Fischette C, Cefalu W, Schade DS (Diabetes Care 1994 Dec; 17(12): 1460–4.), show that sustained release glipizide taken once a day by diabetic patients provides an effective mean glipizide concentration (>50 ng/nl) twenty-four (24) hours after dosing, even at the lowest dosage level of 5 mg. Extended release glipizide was significantly more effective than immediate release glipizide in reducing fasting plasma glipizide (FPL) levels. Both the immediate release and sustained formulations of glipizide equally reduced postprandial plasma glipizide levels. Glipizide-GITS, however, exerted its control in the presence of lower plasma glipizide concentration in comparison to the concentration of plasma glipizide in patients who ingested the immediate release glipizide. The sustained release glipizide also showed significantly lower insulin and C-peptide levels. This suggests that Glipizide-GITS improves insulin sensitivity.

What is needed is a pharmaceutical composition for the sustained release of glipizide that is relatively simple to manufacture on a commercial level and is also relatively inexpensive.

What is also needed is an efficient delivery system for sustained release glipizide.

What is also needed is a pharmaceutical composition for the sustained release glipizide that releases glipizide in conformity to a zero order kinetics.

What is further needed is a pharmaceutical composition for the sustained release of glipizide that is effective at low plasma glipizide levels.

What is further needed is a pharmaceutical composition for the sustained release of glipizide that is effective at low insulin and C-peptide levels.

What is further needed is a pharmaceutical composition for the sustained release of glipizide that tends to increase insulin sensitivity.

What is further needed is a pharmaceutical composition for the sustained release of glipizide that may be produced in granulated, powder, tablet, slug and/or capsule (including caplet) form.

What is further needed is a method to manufacture a sustained release glipizide composition that results in a composition that meets one or more of the above-described characteristics.

BRIEF SUMMARY OF THE INVENTION

The present invention provides a simple, cost effective and efficient delivery system for sustained release glipizide on a commercial scale which results in a pharmaceutical composition that exhibits substantially the same therapeutic effect as presently available glipizide compositions.

The present invention provides a monolithic matrix system for glipizide using hydrocolloid forming agents. The hydrocolloid forming agent is at least about 50% of the matrix weight. Glipizide is insoluble in water and when fabricated into matrix sustained release preparations, results in a release rate that is mainly dependent on the dissolution rate of the matrix rather than dependent on the diffusion through the matrix. In order to achieve an approximately zero order release rate (a linear constant release rate) over a prolonged period of time, a slow swelling composition with simultaneous erosion of the matrix of the composition is necessary. In the present invention selection of the proper molecular weight of the hydrophilic polymer and degree of substitution and combinations thereof is important for attaining an approximately zero order release rate of glipizide though the matrix. The hydrophilic polymers and their combinations are chosen to equate the swelling rate of the polymer matrix to the dissolution rate of the polymer, thereby causing the release of glipizide predominantly by erosion and dissolution. The process of producing the sustained release composition, in one embodiment, comprises granulating glipizide, hydrophylic polymer and a diluent, drying the product and then lubricating it with a flow regulating agent and lubricant.

For a better understanding of the present invention, reference is made to the following description and accompanying figures, while the scope of the invention is set forth in the appended claims.

BRIEF DESCRIPTION OF THE FIGURES

FIG. 4 is a graph of plasma glipizide concentration over a period of twenty-four hours for oral administration of the present invention containing 5 mg. glipizide.

DETAILED DESCRIPTION OF THE INVENTION

Figure 1:
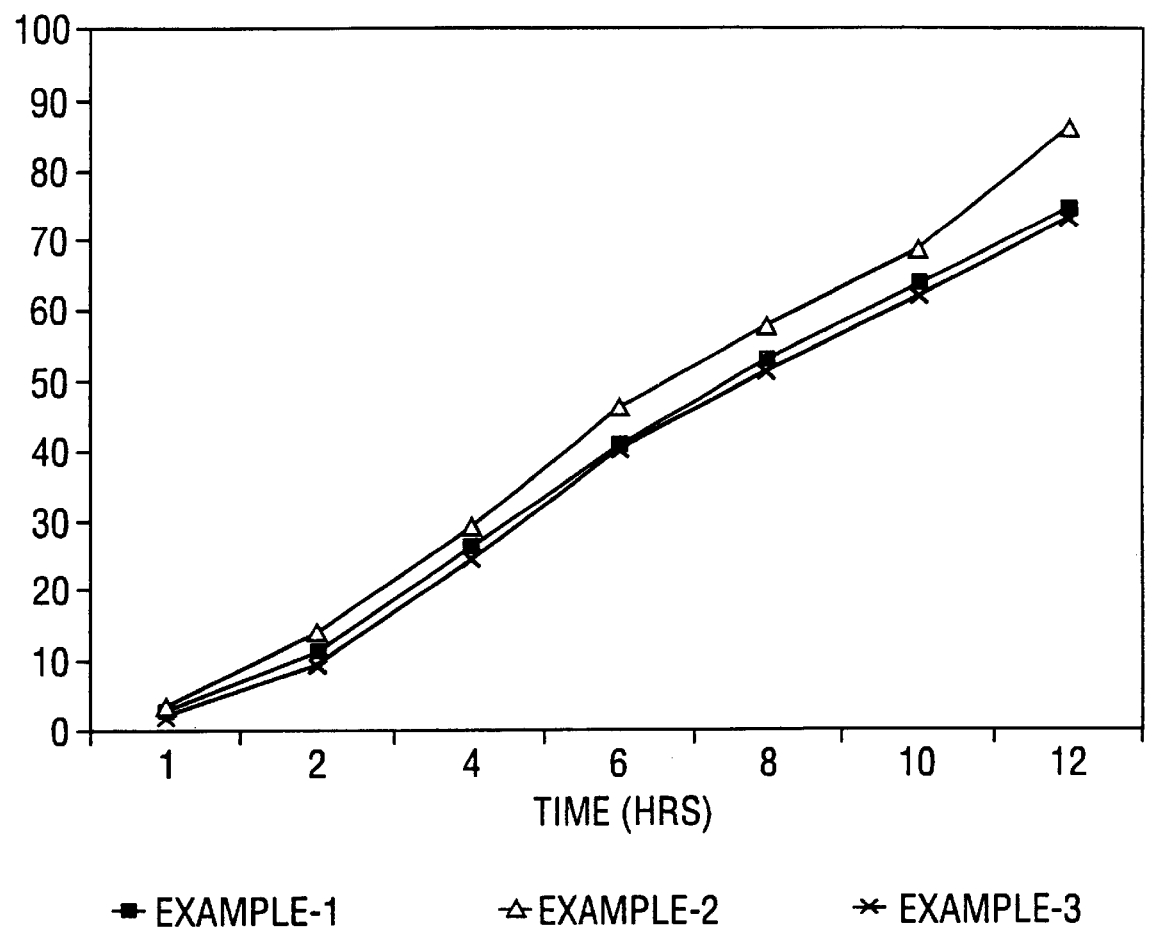
FIG. 1 is a graph of the dissolution rate of glipizide in Examples 1 to 3 of the invention.

The present invention provides a monolithic matrix system for the sustained release of glipizide using hydrocolloid forming agents and other auxiliary excipients. Hydrophilic polymers that may be employed for the monolithic sustained release system in the present invention include, but are not limited to, hydroxypropyl methyl cellulose (Methocel®), hydroxypropyl cellulose (Klucel®), sodium carboxy methyl cellulose and their mixtures. The mixtures of the hydrophilic polymers in weight ratio to the other hydrophilic polymers are within the range of about 1:12 to 12:1, and preferably within the range of about 1:6 to 6:1.

In the present invention the preferred hydrophilic polymer includes hydroxypropyl methyl cellulose with an average molecular weight in the range of 20,000 to 120,000, preferably 26,000 to 86,000 with a methoxy degree of substitution ranging from 1.36 to 1.90 and hydroxypropyl molar substitution ranging from 0.18 to 0.25.

Another suitable hydrophilic polymer is hydroxypropyl cellulose having a molecular weight in the range of 80,000 to 115,000, preferably from 80,000 to 85,000. Also a combination of the different molecular weights of the same polymer and/or different polymers can be employed where the weight ratio is in the range of about 1:12 to 12:1, and preferably within the range of about 1:6 to 6:1.

Auxiliary substances which may be used in the monolithic sustained release matrix system of the present invention include diluents including lactose, microcrystalline cellulose, dicalcium phosphate, polyvinyl pyrrolidone, gelatin, gum acacia, Klucel® EF (hydroxypropyl cellulose), and carboxymethyl cellulose sodium. The flow regulating agents include colloidal silicone dioxide, talc, starch, and others known in the art. The lubricants include magnesium stearate and zinc stearate. For each of the diluents, flow regulating agents and lubricants, others known in the art may also be used.

The pharmaceutical compositions according to the present invention can be used to produce compressed tablets of any shape and are preferably round or formed into compressed compact slugs and filled into capsules using available capsule filling machines.

In the present invention, the pharmaceutical dosage tabletized form, apart from the active drug and hydrophilic polymers and/or other hydrophilic substance, may contain 5 to 50% by weight of a diluent, preferably in the range of about 10 to 40% by weight; a binder, in the range of about 1.0 to 15% by weight, preferably 3.0 to 10% by weight; up to 2.0% by weight of a glidant preferably 0.5 to 1.0% by weight; and up to 2.0% by weight of a lubricant and preferably in the range of about 0.5 to 1.0% by, each of these percentages in relation to the tablet or capsule weight.

In the present invention the pharmaceutical composition, such as tablets, is produced by dry mixing of the active substance, the hydrophilic polymers and optionally other auxiliary substance(s). This mixture is then granulated with an aqueous or organic solution and with a binder followed by drying and converting the granulated mixture into 30 μm to 1.5 mm granules, preferably 100 μm to 1.0 mm through milling and sizing. Thereafter auxiliary substances may be admixed with the converted granules.

In the present invention the pharmaceutical composition, such as tablets, is also produced by the dry mixing (direct compression) of the active substance, hydrophilic polymers, and optionally auxiliary substances such as a diluent(s), binder(s), flow regulating agent(s), and/or lubricant(s). The composition produced in this manner is subsequently processed in the usual manner to produce pharmaceutical dosage forms, e.g., compressed into tablets or filling of pressed compact slugs into capsules.

The sustained release tablets/capsules according the present invention release glipizide in a controlled manner which provides an effect over a time period up to 24 hours, and preferably for more than 18 hours.

Glipizide sustained release formulations in accordance with the present invention show the following in vitro drug release characteristics when tested in gastric fluid pH 1.2 for the first hour and then in phosphate buffer pH 6.8 USP.

| Time Hr | % Release |
| --- | --- |
| 1 | 2–4% |
| 2 | 9–13% |
| 4 | 23–29% |
| 6 | 37–45% |
| 8 | 48–58% |
| 10 | 59–69% |
| 12 | 72–85% |

An in vivo bioavailability study conducted on 12 healthy volunteers with sustained release tablets of the present invention containing 5 mg glipizide, shows well sustained plasma levels of glipizide over 24 hours with 50 to 60 ng/ml plasma concentration of glipizide after 24 hours. As suggested in the literature, the commercially available Glipizide-GITS system, is able to offer a sustained plasma levels of glipizide over 24 hours with the above-referenced plasma glipizide and C-peptide levels. The present invention achieves plasma glipizide levels similar to those achieved by Glipizide-GITS 5 mg tablets and provides a much simpler way of formulating the same preparation in yet a relatively more economical and viable manner. This preparation can be made easily by utilizing known polymers and available equipment, proving its efficiencies over the costly and more difficult to make preparations of Glipzide-GITS. A discussion of several examples employing the pharmaceutical composition of the present invention follows.

EXAMPLE 1

50 gm glipizide was mixed with 760 gm of Methocel® K 100 LV, 200 gm of Methocel® K-4M and 310 gm of lactose monohydrate. Each of these substances is readily available. The resulting mixture was granulated with a solution of 50 gm polyvinyl pyrrolidone in 800 gm isopropyl alcohol. The resulting dough mass was dried at 45° C. for two hours and then sized through 2.4 mm screen to break the agglomerates. These sized granules (1370 gm) were blended with 10 gm of colloidal silicone dioxide, 10 gm of talc and 20 gm of magnesium stearate and compressed into round tablets of each containing 5 mg of glipizide.

The in vitro release of glipizide from these tablets was tested in hydrochloric acid solution at pH 1.2 for the first hour and then continued in phosphate buffer pH 6.8 U.S.P. The results shown in FIG. 1 show a substantially zero order kinetics release of glipizide throughout a twelve hour period.

In vivo bioavailability studies were performed on twelve (12) healthy human volunteers after oral administration of Glipizide SR tablet of Example 1 containing 5 mg of glipizide as per the present invention. The plasma glipizide concentration versus time over twenty-four hours indicates the relatively low levels of plasma glipizide concentration at various intervals during a twenty-four hour period. A graph of plasma levels versus time is shown in FIG. 4. It shows the relatively low levels of glipizide plasma levels after 24 hours. Other parameters are shown below.

| Parameter | Glipizide SR tablet of Example 1 containing 5 mg of glipizide |
| --- | --- |
| AUC (0–24) | 4181 ng/ml × min (±380) |
| C max | 415.7 ng/ml ± 22.75 |
| T max | 5.67 Hrs. ± 1.37 |

The single dose in vivo bioavailability study shows well sustained plasma levels of glipizide over 24 hours with 50 to 60 ng/ml plasma concentration of glipizide after 24 hours.

EXAMPLE 2:

50 gm glipizide was mixed with 760 gm of Methocel® K 100 LV, 200 gm of Methocel® K-4M and 310 gm of lactose monohydrate. The resulting mixture was granulated with solution of 50 gm polyvinyl pyrrolidone in 800 gm isopropyl alcohol. The resulting dough mass was dried at 45° C. for two hours and then sized through 2.4 mm screen to break the agglomerates. These sized granules (1370 gm) were blended with 10 gm of colloidal silicone dioxide, 10 gm of talc and 20 gm of magnesium stearate and compressed into slugs and filled into size 2 capsules.

The in vitro release of glipizide from these capsules was tested in hydrochloric acid solution pH 1.2 for first hour and then continued in phosphate buffer pH 6.8 U.S.P. The result is depicted in FIG. 1 which shows a substantially zero order kinetics release of glipizide throughout a twelve hour period.

EXAMPLE 3

50 gm glipizide was mixed with 760 gm of Methocel® K® 100 LV, 180 gm of Klucel(® HXF and 310 gm of lactose monohydrate. The resulting mixture was granulated with solution of 50 gm polyvinyl pyrrolidone in 800 gm isopropyl alcohol. The resulting dough mass was dried at 45° C. for two hours and then sized through 2.4 mm screen to break the agglomerates. These sized granules (1350 gm) were blended with 10 gm of colloidal silicone dioxide, 10 gm of talc and 20 gm of magnesium stearate and compressed into round tablets each containing 5 mg of glipizide.

The in vitro release of glipizide from these tablets was tested in hydrochloric acid solution pH 1.2 for the first hour and then continued in phosphate buffer pH 6.8 U.S.P. The result is depicted in FIG. 1 which shows a substantially zero order kinetics release of glipizide throughout a twelve hour period.

EXAMPLE 4

50 gm glipizide was mixed with 800 gm of Klucel®-GF, 190 gm of Klucel®-MF and 300 gm of lactose monohydrate. The resulting mixture was granulated with solution of 50 gm polyvinyl pyrrolidone in 800 gm isopropyl alcohol. The resulting dough mass was dried at 45° C. for two hours and then sized through 2.4 mm screen to break the agglomerates. These sized granules (1390 gm) were blended with 10 gm of colloidal silicone dioxide, 10 gm of talc and 20 gm of magnesium stearate and compressed into round tablets each containing 5 mg of glipizide.

Figure 2:
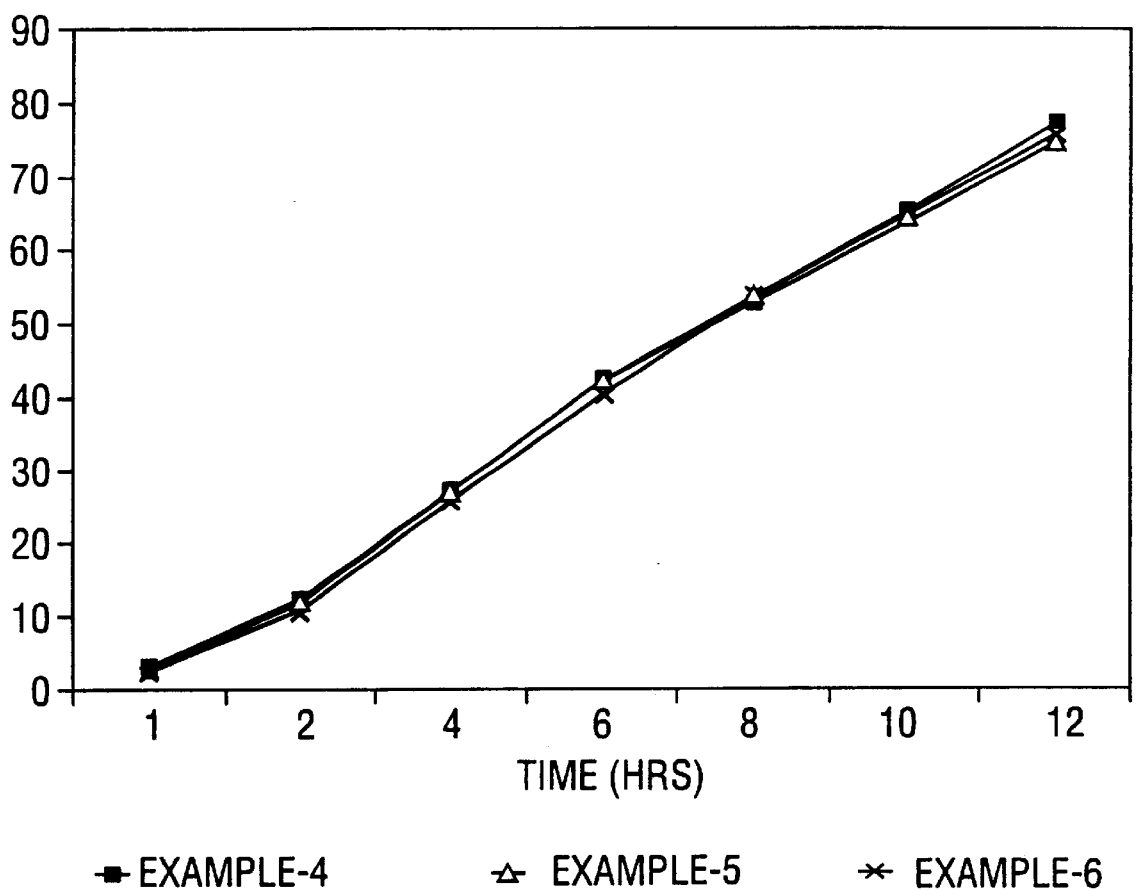
FIG. 2 is a graph of the dissolution rate of glipizide in Examples 4 to 6 of the invention.

The in vitro release of glipizide from these tablets was tested in hydrochloric acid solution pH 1.2 for the first hour and then continued in phosphate buffer pH 6.8 U.S.P. FIG. 2 shows the results which is a substantially zero order kinetics release of glipizide throughout a twelve hour period.

EXAMPLE 5

100 gm glipizide was mixed with 1600 gm of Methocel® K 100 LV, 400 gm of Methocel® K-4M and 600 gm of lactose monohydrate. The resulting mixture was granulated with solution of 100 gm polyvinyl pyrrolidone in 800 gm isopropyl alcohol. The resulting dough mass was dried at 45° C. for two hours and then sized through 2.4 mm screen to break the agglomerates. The sized granules (2800 gm) were blended with 15 gm of colloidal silicone dioxide, 15 gm of talc and 20 gm of magnesium stearate and compressed into round tablets of each containing 10 mg of glipizide.

The in vitro release of glipizide from these tablets was tested in hydrochloric acid solution pH 1.2 for the first hour and then continued in phosphate buffer pH 6.8 U.S.P. FIG. 2 shows the result which is a substantially zero order kinetics release of glipizide throughout a twelve hour period.

EXAMPLE 6

200 gm glipizide was mixed with 3000 gm of Methocel® K 100 LV, 800 gm of Methocel® K-4M and 1000 gm of lactose monohydrate. The resulting mixture was granulated with solution of 100 gm polyvinyl pyrrolidone in 1600 gm isopropyl alcohol. The resulting dough mass was dried at 45° C. for two hours and then sized through 2.4 mm screen to break the agglomerates. The sized granules (5100 gm) were blended with 30 gm of colloidal silicone dioxide, 30 gm of talc and 40 gm of magnesium stearate and compressed into round tablets each containing 20 mg of glipizide.

The in vitro release of glipizide from these tablets was tested in hydrochloric acid solution pH 1.2 for the first hour and then continued in phosphate buffer pH 6.8 U.S.P. FIG. 2 shows the result which is a substantially zero order kinetics release of glipizide throughout a twelve hour period.

EXAMPLE 7

25 gm glipizide was mixed with 550 gm of Methocel® K 100 LV, 140 gm of Methocel® K-4M and 220 gm of lactose monohydrate. The resulting mixture was granulated with solution of 30 gm polyvinyl pyrrolidone in 570 gm isopropyl alcohol. The resulting dough mass was dried at 45° C. for two hours and then sized through 2.4 mm screen to break the agglomerates. The sized granules (965 gm) were blended with 8 gm of colloidal silicone dioxide, 8 gm of talc and 15 gm of magnesium stearate and compressed into round tablets of each containing 2.5 mg of glipizide.

Figure 3:
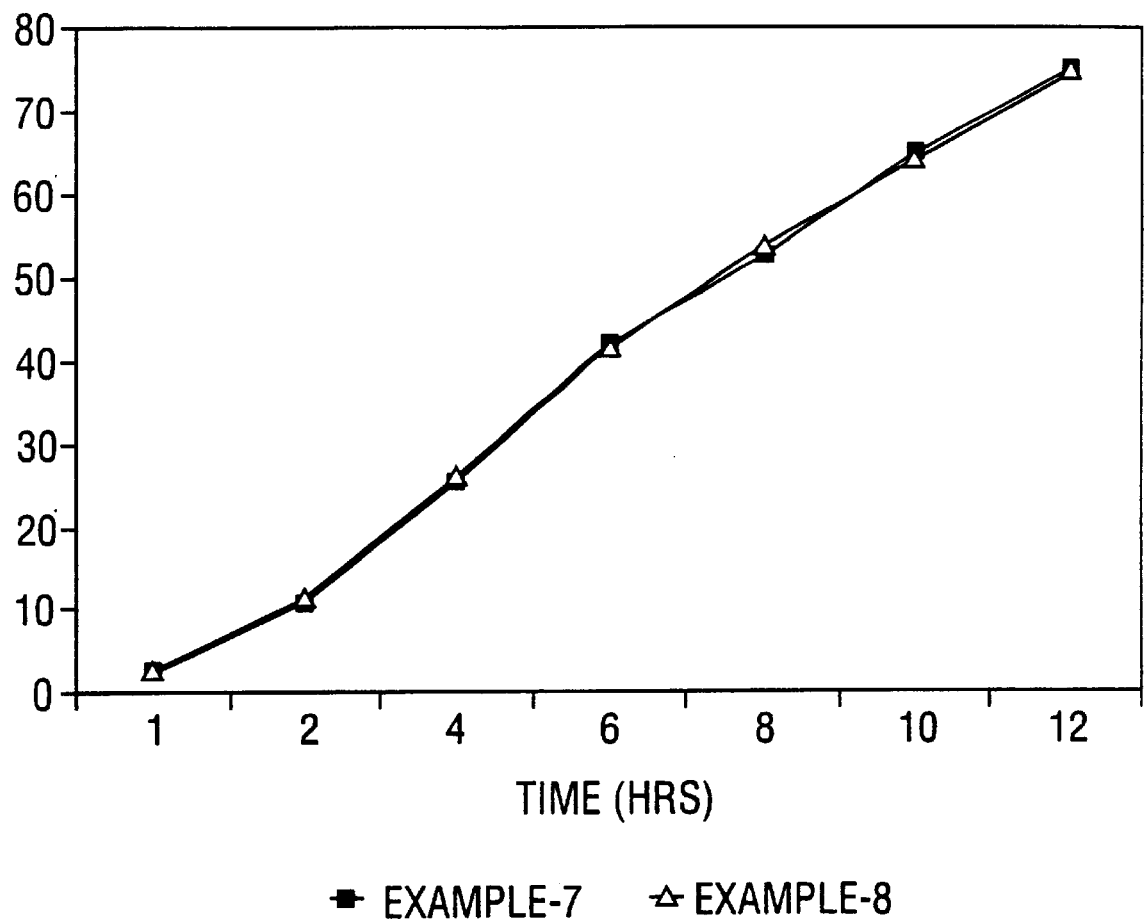
FIG. 3 is a graph of the dissolution rate of glipizide in Examples 7 and 8 of the invention.

The in vitro release of glipizide from these tablets was tested in hydrochloric acid solution pH 1.2 for the first hour and then continued in phosphate buffer pH 6.8 U.S.P. FIG. 3 shows the result which is a substantially zero order kinetics release of glipizide throughout a twelve hour period.

EXAMPLE 8

Direct Compression 50 gm glipizide was mixed with 760 gm of Methocel® K 100 LV, 200 gm of Methocel® K-4M and 310 gm of lactose monohydrate., 50 gm of polyvinyl pyrrolidone, 10 gm of colloidal silicone dioxide, 10 gm of talc and 20 gm of magnesium stearate and compressed into round tablets each containing 5 mg of glipizide.

The in vitro release of glipizide from these tablets was tested in hydrochloric acid solution pH 1.2 for the first hour and then continued in phosphate buffer pH 6.8 U.S.P. FIG. 3 shows the result which is a substantially zero order kinetics release of glipizide throughout a twelve hour period.

While the foregoing represent the preferred compositions of the present invention, it is understood that various modifications from those described herein will be apparent to one skilled in the art without departing from the spirit and scope of the invention.

What is claimed is:

1. A sustained release glipizide composition that releases glipizide in conformity to a zero-order kinetics and results in a serum plasma glipizide concentration of at least 50 ng/ml twenty-four hours after administration of a single dose of said composition, comprising:
    a. glipizide in an amount from 2–5 percent by weight;
    b. at least one hydrophilic polymer selected from a group consisting of hydroxypropylmethylcellulose having a molecular weight of 26,000–86,000, a methoxy degree of substitution of 1.36–1.90, and a hydroxypropyl molar substitution of 0.18–0.25, and hydroxypropylcellulose having a molecular weight of 80,000–115,000, in an amount from 65–75 percent by weight;
    c. a diluent selected from a group consisting of polyvinylpyrrolidone, microcrystalline cellulose and gum arabic, in an amount from 1.5–4.0 percent by weight;
    d. at least one flow regulating agent selected from a group consisting of colloidal silicon dioxide, talc and starch, in an amount from 1–2 percent by weight;
    e. a lubricant selected from a group consisting of magnesium stearate and zinc stearate, in an amount from 0.5–1.5 percent by weight; and
    f. at least one other excipient, in a percentage amount by weight such that a total weight of said composition is 100 percent;
   said composition further comprising an oral dosage form having from 2.5–20 mg glipizide.

2. The composition of claim 1, wherein said composition is in a form selected from a group consisting of a tablet, a slug, a capsule, a caplet and a granular form.

3. A process of producing a sustained release glipizide composition that releases glipizide in conformity to a zero-order kinetics and results in a serum plasma glipizide concentration of at least 50 ng/ml twenty-four hours after administration of a single dose of said composition, comprising the steps of:
    a. mixing glipizide with at least one hydrophilic polymer selected from a group consisting of hydroxypropylmethylcellulose having a molecular weight of 26,000–86,000, a methoxy degree of substitution of 1.36–1.90, and a hydroxypropyl molar substitution of 0.18–0.25, and hydroxypropylcellulose having a molecular weight of 80,000–115,000, and at least one other excipient, to form a mixture;
    b. granulating the mixture with a diluent selected from a group consisting of polyvinylpyrrolidone, microcrystalline cellulose and gum arabic, and an alcohol;
    c. drying the granulated mixture;
    d. sizing the dried granulated mixture through a 2.4 mm screen to form sized granules;
    e. blending the sized granules with at least one flow regulating agent selected from a group consisting of colloidal silicon dioxide, talc and starch, and a lubricant selected from a group consisting of magnesium stearate and zinc stearate; and
    f. compressing the blended sized granules into a plurality of oral dosage forms, each form containing glipizide in an amount from 2.5–20 mg.

4. The process as in claim 3, further comprising forming the composition to have a form selected from a group consisting of a tablet, a slug, a capsule, a caplet and a granular form.

5. A process of producing a sustained release glipizide composition that releases glipizide in conformity to a zero-order kinetics and results in a serum plasma glipizide concentration of at least 50 ng/ml twenty-four hours after administration of a single dose of said composition, comprising the steps of:
   a. mixing glipizide with at least one hydrophilic polymer selected from a group consisting of hydroxypropylmethylcellulose having a molecular weight of 26,000–86,000, a methoxy degree of substitution of 1.36–1.90, and a hydroxypropyl molar substitution of 0.18–0.25, and hydroxypropylcellulose having a molecular weight of 80,000–115,000; a diluent selected from a group consisting of polyvinylpyrrolidone, microcrystalline cellulose and gum arabic; at least one flow regulating agent selected from a group consisting of colloidal silicon dioxide, talc and starch; a lubricant selected from a group consisting of magnesium stearate and zinc stearate; and at least one other excipient; and
   b. compressing the mixture into a plurality of oral dosage forms, each form containing glipizide in an amount from 2.5–20 mg.

6. The process as in claim 5, further comprising forming the composition to have a form selected from a group consisting of a tablet, a slug, a caplet and a granular form.

* * * * *